(12) United States Patent
Bonningue et al.

(10) Patent No.: US 7,651,464 B2
(45) Date of Patent: Jan. 26, 2010

(54) APPARATUS FOR SEARCHING FOR AND DETECTING DEFECTS IN PARTS BY ENDOSCOPY

(75) Inventors: Isabelle Bonningue, Soisy sur Seine (FR); John LeQuellec, Vaux le Penil (FR); Jean-Claude Lemoal, La Brosse Hericy (FR); Michel Baccella, Villiers sur Orge (FR)

(73) Assignees: Snecma, Paris (FR); Snecma Services, Paris (FR)

( * ) Notice: Subject to any disclaimer, the term of this patent is extended or adjusted under 35 U.S.C. 154(b) by 0 days.

(21) Appl. No.: 10/880,502

(22) Filed: Jul. 1, 2004

(65) Prior Publication Data

US 2005/0200842 A1 Sep. 15, 2005

(30) Foreign Application Priority Data

Jul. 4, 2003 (FR) .................................. 03 08156

(51) Int. Cl.
*A61B 1/06* (2006.01)
(52) U.S. Cl. .................. 600/164; 600/113; 600/153; 600/156; 600/158; 600/160; 600/310; 600/311; 600/312; 600/427; 600/476; 356/51; 356/241.1; 356/241.5; 356/927; 356/928; 250/365
(58) Field of Classification Search ............ 600/160, 600/164, 310–317, 113, 476; 607/94
See application file for complete search history.

(56) References Cited

U.S. PATENT DOCUMENTS 3,456,641 A * 7/1969 Matsuo et al. .............. 600/109
3,995,157 A * 11/1976 Holub et al. ................ 250/302
4,273,110 A * 6/1981 Groux ....................... 600/156
4,628,207 A * 12/1986 Elfert et al. .............. 250/461.1
4,784,118 A * 11/1988 Fantone et al. ............. 600/160
4,784,135 A 11/1988 Blum et al.
5,014,709 A * 5/1991 Bjelkhagen et al. ........ 600/431
5,046,845 A * 9/1991 Diener .................... 356/239.7
5,115,136 A * 5/1992 Tomasch ................ 250/461.1
5,170,775 A * 12/1992 Tagami .................... 356/241.4
5,486,641 A * 1/1996 Shum et al. .................. 558/78
5,881,195 A * 3/1999 Walker ....................... 385/116
5,900,971 A * 5/1999 Ning ........................ 359/435
6,400,980 B1 6/2002 Lemelson
6,876,446 B2 * 4/2005 Taylor et al. ............. 356/241.1
2002/0193664 A1 * 12/2002 Ross et al. .................. 600/178
2003/0050534 A1 * 3/2003 Kazakevich ................ 600/178
2005/0085698 A1 4/2005 Bonningue et al.

\* cited by examiner

*Primary Examiner*—Matthew J Kasztejna
(74) *Attorney, Agent, or Firm*—Oblon, Spivak, McClelland, Maier & Neustadt, L.L.P.

(57) ABSTRACT

Apparatus for searching for and detecting defects on parts that are substantially inaccessible, being located behind a wall, the apparatus comprising a first endoscope for illumination in visible light and for observation, the first endoscope and pipes for feeding and spraying penetration test substances being housed together in a rod which can be passed through an orifice in the wall in order to examine a part, the apparatus further comprising a second endoscope independent of the first endoscope and the rod for illuminating in ultraviolet light and for observing the portion of the part that has been treated by the penetration test substances.

28 Claims, 2 Drawing Sheets

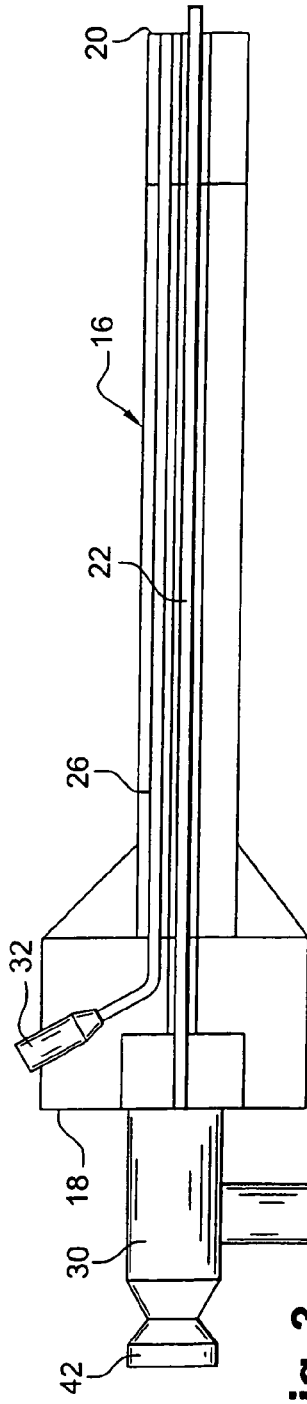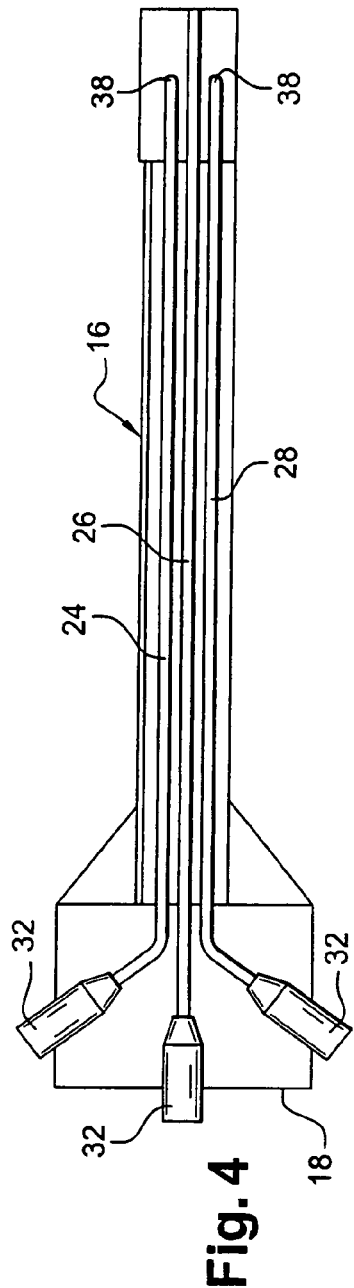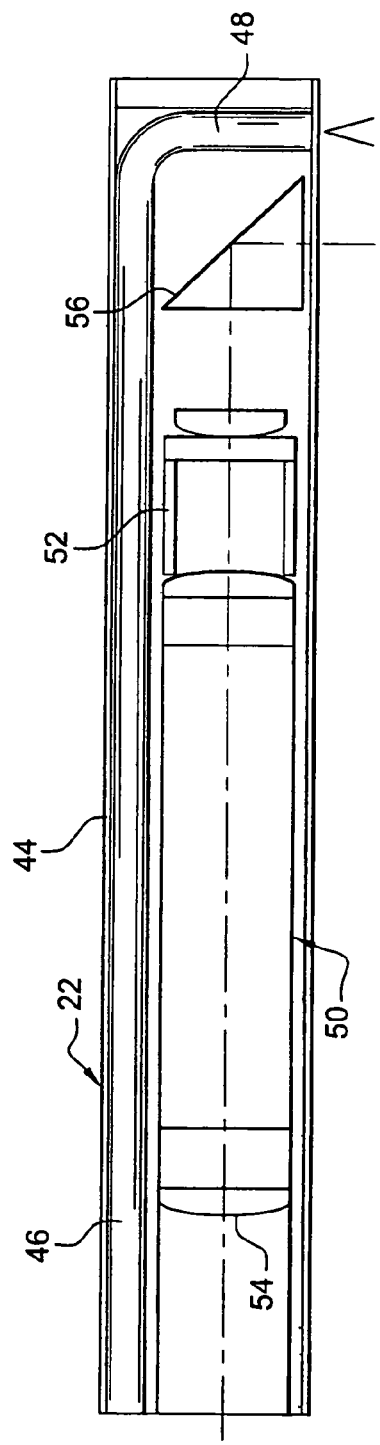

APPARATUS FOR SEARCHING FOR AND DETECTING DEFECTS IN PARTS BY ENDOSCOPY

The invention relates to endoscopic apparatus for searching for and detecting defects in parts that are substantially inaccessible, being located behind a wall.

BACKGROUND OF THE INVENTION

It is already known to inspect internal components of equipment or a machine by means of an endoscope, i.e. an elongate optical instrument of small diameter that is passed through a small orifice in a wall in order to examine the appearance of components that are located on the other side of the wall. This makes it possible in particular to inspect the blades of a turbomachine such as an airplane turbojet or turboprop, without dismantling the turbomachine.

Nevertheless, the ability to detect defects is limited by the resolution of the optical system of the endoscope, by the illumination, by the orientation of the endoscope relative to the surface under observation, and by the nature of the defects, amongst other things.

It is also known to seek defects on machine components by using a penetration test technique, which consists in depositing organic substances on the surface under examination of a component and in observing the results under ultraviolet illumination. It is thus possible to detect surface discontinuities such as cracks or fissures that are of very small dimensions, and that are invisible under normal illumination, by depositing a fluorescent dye on the component, which dye penetrates into the surface discontinuities, and then by washing and baking or drying the corresponding surface of the component, and subsequently depositing a developer to reveal the fluorescent dye that has infiltrated into the surface discontinuities. The component is then illuminated in ultraviolet radiation which excites the fluorescent dye, which responds by emitting radiation at some other wavelength, for example of a green color in the visible spectrum.

This penetration test technique generally requires the machine under examination to be disassembled more or less completely.

Proposals have already been made, in document U.S. Pat. No. 4,273,110, to combine the techniques of endoscopy and of penetration testing in a single instrument which comprises, in an elongate cylindrical sheath of small diameter, a quartz tube for transmitting ultraviolet light and visible light towards an end of the instrument that is close to the component under examination, a light pipe containing lenses to observe an illuminated zone of the component, and three pipes for feeding and spraying penetration test substances onto the component under examination. An optical filter that stops visible light is removably mounted at the other end of the instrument between the quartz tube and a light source that emits in the visible and in the ultraviolet, so as to enable the component to be illuminated alternately in visible light and in ultraviolet light. The outside diameter of the sheath of the instrument is small enough to enable it to pass through an endoscope orifice having a diameter of about 9 millimeters (mm).

That prior art instrument presents several drawbacks:

The illumination of the component in ultraviolet light takes place via an axial outlet in order to avoid using reflecting mirrors which are excessively penalizing in terms of size and light absorption. The outlets of the spray pipes are necessarily axial, as are the outlets for illumination and for the observation means, thereby greatly restricting the use of the instrument. In addition, the section of the observation light pipe is very small, since said pipe must leave sufficient space inside the sheath to enable the quartz tube and the pipes for feeding and spraying penetration test substances to be installed, such that when the instrument is used with ultraviolet illumination, it can pick up only a small fraction of the light emitted by the penetration test substances, and therefore does not enable observation to be performed reliably.

OBJECTS AND SUMMARY OF THE INVENTION

A particular object of the invention is to provide a solution to this problem which is simple, satisfactory, and inexpensive.

The invention seeks to provide apparatus combining the techniques of endoscopy and penetration testing, while avoiding the drawbacks of known means.

To this end, the invention provides apparatus for searching for and detecting defects on parts that are substantially inaccessible, being located behind a wall, the apparatus comprising a rigid tubular cylindrical rod of small diameter for passing through an endoscope orifice in the wall, pipes received in the rod for depositing penetration test substances on a portion of the part under examination, and light guide and image transmission means received in the rod to illuminate and observe said portion of the part under examination, wherein the light guide and image transmission means are constituted by a first endoscope that operates with visible light mounted axially in the rod and surrounded by pipes for air and penetration test substances, said endoscope having a tube that is rectilinear in which the visible light guide means and the image transmission means are mounted in parallel, and wherein the apparatus further comprises a second endoscope that operates with ultraviolet light, independent of the first endoscope and of the above-mentioned rod for observing the portions of the part that has been treated by the penetration test substances.

In the apparatus of the invention, it is the visible light endoscope that is housed together with the pipes for penetration test substances in the cylindrical rod, which is used solely for observation in visible light of the portion of the part onto which the test substances have been sprayed. The effects of these substances are then observed by means of the second endoscope whose optical performance is not restricted by its cross-section being reduced because of the presence of pipes for feeding test substances being housed in a tube of dimensions that are small enough to allow it to be passed through an endoscope orifice.

Illuminating the portion of the part that is to be treated in visible light suffices to ensure that the test substances are properly deposited, and illuminating said portion of the part in ultraviolet light by means of the second endoscope makes it possible to observe clearly the effects of the test substances, thereby optimizing detection of defects in the parts under examination.

According to another characteristic of the invention, the light guide means of the first endoscope comprise an optical fiber cable extending from one end to the other of the tube, the cable having a bent outlet end that is oriented obliquely relative to the axis of the tube and that is for bringing into the vicinity of a portion of a part that is to be examined.

The illumination outlet is thus not axial, but is perpendicular to the axis of the tube, for example, so turning the rod about its own axis, and moving said rod in translation along its axis makes it possible to illuminate and observe large areas of the parts.

The image transmission means of the first endoscope comprise a rectilinear set of optical components, comprising an image-forming objective lens and image-transferring lenses, said set extending from one end of the tube to the other and also comprising light reflector means mounted at the end of said set of components on its optical axis and oriented obliquely relative to said optical axis.

These optical reflector means and the bent outlet end of the illuminating cable are close together and are oriented in corresponding manner so as to illuminate and observe the same portion of the part.

Preferably, the optical reflector means are formed by a prism.

The reflecting face of the prism is advantageously oriented at 45° relative to the optical axis of the image transmission means and the bent end of illuminating cable extends perpendicularly to the axis of the tube.

The pipes which are received in the rod around the first endoscope comprise an air pipe, a powder pipe, and a liquid pipe, extending from one end of the rod to the other, and each having a first end for connection to feed means. The second ends of the powder and liquid pipes open out at the corresponding end of the rod in the same direction as the illuminating means and the image transmission means of the first endoscope, whereas the second end of the air pipe opens out axially at the end of the rod in order to protect the first endoscope and prevent powder and liquid becoming deposited on its end.

In a particular embodiment of the invention, the tube of the first endoscope has a diameter of about 4 millimeters (mm) and the rod has a diameter of about 8 mm.

The second endoscope for illuminating in ultraviolet light can have an outside diameter that is substantially equal to that of the above-mentioned rod, thus ensuring good performance in terms of illumination in ultraviolet light and observation of defects in the part.

BRIEF DESCRIPTION OF THE DRAWINGS

The invention will be better understood and other characteristics, details, and advantages thereof will appear more clearly on reading the following description made by way of example with reference to the accompanying drawings, in which:

FIGS. 3 and 4 are diagrammatic plan views of the rod for illuminating in visible light and for depositing penetration test substances; and FIG. 5 is a diagrammatic axial section view of the visible light endoscope used in this rod.

MORE DETAILED DESCRIPTION

Figure 1:
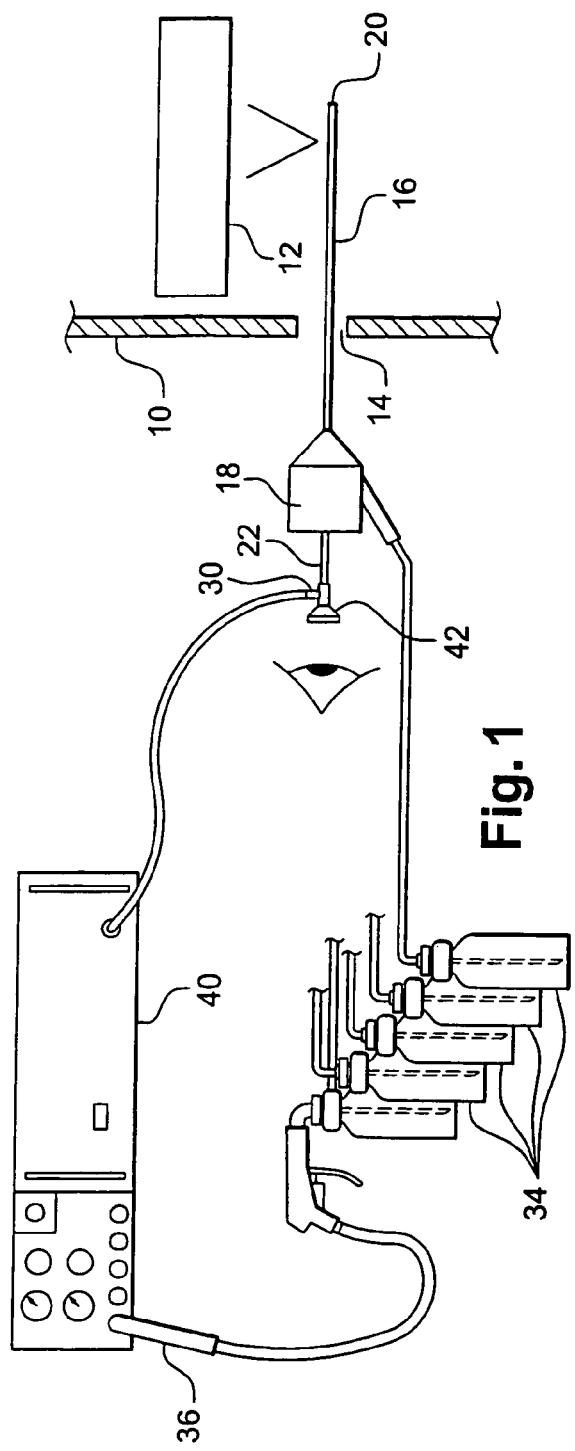
FIG. 1 is a diagrammatic view of the apparatus of the invention for illuminating with visible light and depositing penetration test substances onto the part to be examined.

In FIG. 1, reference 10 designates a wall such as a turbomachine casing behind which there are parts 12 for examination such as the rotor blades of the turbomachine.

The wall 10 includes an endoscope orifice 14 of small size (typically having a diameter of 9 mm), through which it is possible to insert a rod 16 for illuminating with visible light and for spraying penetration test substances, one end of the rod being provided with a block 18 for connection to means for supplying penetration test substances and compressed air, and its other end 20 being designed to be brought up to face a surface of the part 12 for examination.

The rod 16 is shown in greater detail in FIGS. 3 and 4. The rod is a rigid tubular cylinder, e.g. made of metal, and contains a first endoscope 22 for illuminating and observing in visible light, a pipe 24 for feeding and spraying a powder on the surface of the part 12 to be examined, a pipe 26 for feeding compressed air, and a pipe 28 for feeding and spraying a liquid which may be in succession acetone, a penetrating agent, an emulsifier, and water. The first endoscope 22 and the pipes 24, 26, and 28 extend longitudinally in the rod 16 from one end thereof to the other, the endoscope lying on the axis of the rod 16 and the pipes 24, 26, and 28 being disposed around the endoscope.

As shown diagrammatically in FIGS. 1 and 3, the first endoscope 22 has a first end 30 for connection to a source of visible light and a second end which is described in greater detail below and which opens out at the end 20 of the rod 16.

The pipes 24 and 28 for feeding penetration test substances have first ends 32 for connection to tanks 34 containing the substances, themselves connected to a compressed air feed 36, and having second ends 38 which open out at the end 20 of the rod 16 perpendicularly to the axis of said rod.

The compressed air feed means and the sources of visible and ultraviolet light are preferably grouped together in a feed module 40, itself including electrical power supply means and compressed air supply means.

The end 30 of the first endoscope 22 includes an eyepiece 42 enabling an observer to view directly the surface of the part 12 under examination facing the end 20 of the rod.

The endoscope 22 is shown in greater detail in FIG. 5, and it essentially comprises a rigid cylindrical tube 44, e.g. made of metal having disposed therein an optical fiber cable 46 for guiding visible light from one end of the endoscope to the other, the cable 46 having a first end for connection to the visible light source provided in the feed module 40, and a second end 48 through which light is delivered and extending for example perpendicularly to the axis of the tube 44 at the end of the endoscope that is remote from the end fitted with the eyepiece 42. Image transmission means 50 are also disposed inside the tube 44 and extend therein longitudinally from one end to the other, said image transmission means 50 being constituted by a rectilinear assembly of optical components comprising, in particular: an image-forming objective lens 52 and one or more transfer lenses 54. Reflector means 56 are placed in the tube 44 close to the objective lens 52, between said lens and the second end 48 of the light guide means 46, the optical reflector means 56 being formed by a prism which is placed on the optical axis of the image transmission means 50 and which has a reflecting face inclined at 45° relative to said axis, for example, in order to observe in a direction that is perpendicular to said optical axis and parallel to the direction in which the end 48 of the light guide 46 extends.

As can be seen clearly in FIG. 5, the light guide 46 extends along the wall of the tube 44, and the image transmission means 50 occupy practically all of the remainder of the tube, thus making it possible to use a section that is as large as possible for the image transmission means 50 in order to improve observation.

In a particular embodiment, given herein by way of example, the rigid tube 44 has an outside diameter of about 4 mm and a length of about 40 centimeters (cm). It is designed to aim at 90° relative to its axis and to have a field of observation of 55°.

Figure 2:
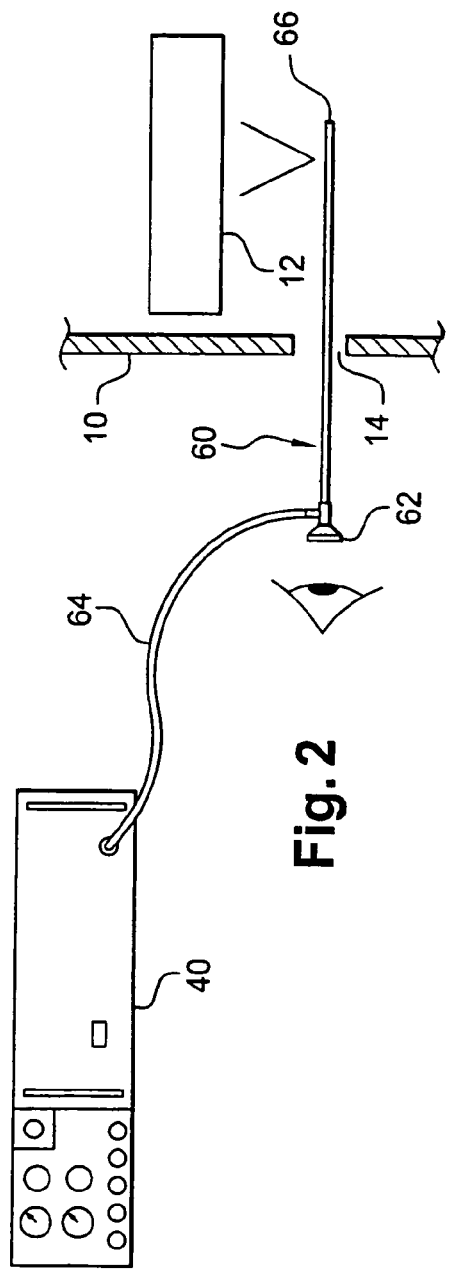
FIG. 2 is a diagrammatic view of the second endoscope for illuminating the part under examination in ultraviolet light.

The apparatus of the invention comprises a second endoscope 60 shown diagrammatically in FIG. 2, which second endoscope is independent from the rod 16 and the first endoscope 22 and is designed to be inserted through the endoscope orifice 14 in the wall 10 in order to observe the surface of the part 12 once it has been treated with the penetration test substances.

This endoscope 60 has a first end provided with an eyepiece 62 and means 64 for connection to a source of ultraviolet light and forming part of the feed module 40, and a second end 66 having a light outlet perpendicular to the axis of the endoscope for illuminating the treated surface of the part 20 in ultraviolet light and for observing it.

This endoscope 60 may be of conventional type, or preferably it is of the type described in another patent application in the name of the Applicant. Since this endoscope 60 is used on its own, it may have transverse dimensions that are larger than would be possible if it were used together with or instead of the first endoscope 22 in the rod 16, which in general means that it is possible to illuminate the surface of the part 12 better in ultraviolet light and to observe the results of the penetration test better.

The apparatus of the invention is used as follows:

Initially, the rod 16 is inserted through the orifice 14 in the wall 10 and its end 20 is moved in axial translation and by being turned about said axis, facing the surface of a part 12 to be examined.

In order to verify whether an apparent defect of the part 12 is or is not a real defect such as a crack or a fissure, penetration test substances are sprayed in succession onto the corresponding portion of the part 12, these substances including a fluorescent liquid which penetrates into surface discontinuities, a washing liquid, and a developer powder for revealing the presence of the penetrating substance that has infiltrated into a surface discontinuity, even if the discontinuity is of very small dimensions.

Examination of the part 12 and observation of the spraying of penetration test substances onto said part are performed using visible light, with the surface of the part 12 being illuminated by the light flux leaving the angled end 48 of the light guide 46 of the first endoscope, this light being reflected and/or backscattered by the surface of the part and being picked up by the mirror 56 which returns it along the axis of the image transmission means 50 to the eyepiece 42 mounted at the other end of the first endoscope.

The rod 16 is then withdrawn from the endoscope orifice 14 and the second endoscope 60 connected to the source of ultraviolet light in the feed module 40 is inserted in turn through the orifice 14 and its end 66 is brought to face the treated surface of the part 12. Illuminating the treated surface of the part 12 in ultraviolet light causes the penetration test substance that has infiltrated into a surface discontinuity and which diffused into the developer to be excited, with the penetrating substance responding to said excitation by fluorescing, e.g. with a green color, which can clearly be seen in the dark and which the user can observe by means of the eyepiece 62.

In general, the separation in accordance with the invention of illumination with ultraviolet light and illumination with visible light makes it possible to improve the performance of both illumination operations and to improve observation of the corresponding results.

What is claimed is:

1. An apparatus for searching for and detecting defects on parts that are substantially inaccessible, being located behind a wall, the apparatus comprising:
   a rigid tubular cylindrical rod including a longitudinal axis and being configured to pass an endoscope through an orifice in the wall;
   pipes positioned in the rod, a plurality of the pipes being configured to deposit penetration test substances on a portion of the part under examination;
   a light guide received in the rod and configured to illuminate the part under examination; and
   first image transmission means received in the rod and configured to allow a user to observe said portion of the part under examination,
   wherein the light guide and the first image transmission means comprise a first endoscope that operates solely with visible light mounted axially in the rod and that is adjacent to the pipes, said first endoscope includes a first tube in which the visible light guide and the first image transmission means are mounted in parallel, the first image transmission means has a diameter greater than that of the light guide,
   wherein the pipes received inside the rod include an air pipe, a powder pipe, and a liquid pipe and extend from a first end of the rod to a second end of said rod opposite the first end of the rod and each pipe has a first end for connection to feed means, the powder and liquid pipes have respective opposite ends that open to an outside of the rod in a same direction as the light guide and the first image transmission means are open, and the air pipe has an opposite end opening out axially at the second end of the rod to generate a flow of air for protecting the end of the first endoscope inside the orifice, and
   said first endoscope is free of any means for producing ultraviolet light; and
   a second endoscope that operates solely with ultraviolet light, independent of the first endoscope and of said rod, configured to allow a user to observe the portion of the part that has been treated by the penetration test substances,
   wherein said second endoscope is free of any pipe for depositing penetration test substances on said portion of the part under examination, and is free of any means for producing visible light, and
   the second endoscope includes,
   a first end provided with an eyepiece,
   a second end opposite the first end and including a light outlet,
   an ultraviolet light guide,
   second image transmission means extending from the first end of the second endoscope along a longitudinal axis of the second endoscope toward the second end of the second endoscope and configured to transmit light to the eyepiece from behind said wall and through the orifice while the first end of the second endoscope is in front of said wall, and
   a second tube with a cylindrical cross-section as viewed along a longitudinal axis of the ultraviolet light guide, the cylindrical cross-section located proximate to the second end, and the ultraviolet light guide and the second image transmission means being disposed within the second tube,
   wherein the light guide and first image transmission means open in a direction transverse to the longitudinal axis of the rod, and
   wherein the ultraviolet light guide and second image transmission means open in a direction transverse to the longitudinal axis of the second endoscope.

2. The apparatus according to claim 1, wherein the light guide of the first endoscope comprises an optical fiber cable extending from one end to the other of the first tube.

3. The apparatus according to claim 2, wherein the optical fiber cable has a bent outlet end oriented obliquely relative to the axis of the first tube and configured to be brought into the vicinity of a portion of the part that is to be illuminated in visible light.

4. The apparatus according to claim 3, wherein the first image transmission means comprise optical reflector means mounted at one end of the first tube on the optical axis of the image transmission means and oriented obliquely relative to said optical axis, and wherein the optical reflector means and the bent outlet end of the optical fiber cable are adjacent and are oriented so as to illuminate and observe respectively a same portion of the part.

5. The apparatus according to claim 4, wherein the optical reflector means are situated between a rectilinear set of optical components and the bent outlet end of the optical fiber cable.

6. The apparatus according to claim 2, wherein the optical fiber cable extends along the wall of the first tube and the first image transmission means occupy substantially the remainder of the tube.

7. The apparatus according to claim 1, wherein the first image transmission means comprise a rectilinear assembly of optical components comprising an image-forming objective lens and image-transferring lenses extending substantially from one end of the first tube to an opposite end of the first tube.

8. The apparatus according to claim 1, wherein the first image transmission means of the first endoscope also comprise optical reflector means mounted at one end of the first tube on the optical axis of the image transmission means and oriented obliquely relative to said optical axis.

9. The apparatus according to claim 8, wherein the optical reflector means include a prism.

10. The apparatus according to claim 8, wherein the optical reflector means have a reflecting surface oriented at 45° relative to the optical axis of the first image transmission means and a bent outlet end of a cable of said light guide extends perpendicularly to the axis of the first tube.

11. The apparatus according to claim 1, wherein the first tube has a diameter of about 4 mm, and the above-mentioned rod has a diameter of about 8 mm.

12. The apparatus according to claim 1, wherein at least one of said first and second endoscopes includes an image transmission means with a diameter that is at least half of an outer diameter of said at least one of said first and second endoscopes.

13. The apparatus according to claim 12, wherein said at least one of said first and second endoscopes is said first endoscope.

14. The apparatus according to claim 1, wherein the ultraviolet light guide and the second image transmission means occupy a majority of a whole internal section of the second tube.

15. The apparatus according to claim 1, wherein the first image transmission means extends along a length of the first endoscope from an eyepiece attached to the first endoscope to an end of the first endoscope opposite the eyepiece.

16. The apparatus according to claim 1, wherein the second tube is rectilinear.

17. The apparatus according to claim 1, wherein the first tube is rectilinear.

18. The apparatus according to claim 1, wherein the cylindrical cross-section of the second tube has an outside diameter substantially equal to an outside diameter of the rod containing the first endoscope.

19. The apparatus according to claim 1, wherein the ultraviolet light guide of the second endoscope is configured to connect to an external light source separate from the second endoscope.

20. A system for searching for and detecting defects on a part, the system comprising:
a rigid tubular cylindrical rod including a longitudinal axis, pipes positioned in said rod, a plurality of said pipes being configured to deposit penetration test substances on a portion of said part,
a first endoscope, which is configured to operate solely with visible light, comprising
a visible light guide with a first diameter, configured to illuminate said portion with visible light, and
a first image transmission mechanism, with a second diameter, configured to transmit an image of said portion being illuminated with said visible light, the first image transmission mechanism and light guide being open in a direction transverse to the longitudinal axis of the rod,
wherein said first endoscope is mounted axially in said rod and is adjacent to said pipes, said visible light guide of said first endoscope has a non-axial outlet configured to outlet said visible light, the second diameter is greater than the first diameter, and the first endoscope is free of any means for producing ultraviolet light; and
a second endoscope including
an ultraviolet light guide extending along a longitudinal axis of the second endoscope, and
a second image transmission mechanism configured to transmit an image of said portion being illuminated with said ultraviolet light and having been treated with said penetration test substances, the second image transmission mechanism extending along the longitudinal axis of the second endoscope from an end of the second endoscope including an eyepiece toward an opposite end of the second endoscope and configured to transmit light to the eyepiece from the opposite end of the second endoscope,
wherein said second endoscope is independent of said first endoscope and of said rod,
wherein said second endoscope is free of any pipe for depositing penetration test substances on said portion,
wherein said second endoscope is further free of any means for producing visible light,
wherein the ultraviolet light guide and second image transmission mechanism open in a direction transverse to the longitudinal axis of the second endoscope, and
wherein the pipes positioned inside the rod include an air pipe, a powder pipe, and a liquid pipe and extend from a first end of the rod to a second end of said rod opposite the first end of the rod and each pipe has a first end for connection to feed means, the powder and liquid pipes have respective opposite ends that open to an outside of the rod in a same direction as the light guide and the first image transmission mechanism open, and the air pipe has an opposite end opening out axially at the second end of the rod to generate a flow of air for protecting the end of the first endoscope inside an orifice.

21. The apparatus according to claim 20, wherein said first image transmission mechanism has a diameter that is at least half of an outer diameter of said first endoscope.

22. The apparatus according to claim 20, wherein the second image transmission mechanism includes a prism.

23. The apparatus according to claim 20, wherein the first image transmission mechanism extends along a length of the first endoscope from an eyepiece attached to the first endoscope to an end of the first endoscope opposite the eyepiece.

24. The apparatus according to claim 20, wherein an outside diameter of a cylindrical cross-section of said second endoscope located proximate to a light outlet of said second endoscope, as viewed along a longitudinal axis of the ultraviolet light guide, is equal to a diameter of said rod.

25. The apparatus according to claim 20, wherein an outside diameter of a cylindrical cross-section of said second endoscope is substantially equal to 8 mm, and an outside diameter of the rod is substantially equal to 8 mm.

26. An apparatus for searching for and detecting defects on a part to be examined that is located behind a wall, the apparatus comprising:

means for inserting a first endoscope into a hole with a first diameter, the means for inserting a first endoscope including
a rod inside which pipes are positioned, the rod including a longitudinal axis, and a plurality of the pipes being configured to deposit penetration test substances on the part to be examined, wherein
the first endoscope, which is free of any means for producing ultraviolet light includes a visible light guide and means for viewing the part while the part is exposed to visible light, the means for viewing including a means for transmitting an image, the means for transmitting an image having a greater diameter than a diameter of the visible light guide, the visible light guide and means for transmitting an image each being open in a direction transverse to the longitudinal axis of the rod; and
means for inserting a second endoscope into the hole after the first endoscope has been inserted into the hole and withdrawn from the hole, the second endoscope being free of any means for depositing penetration test substances on a portion of the part under examination and free of any means for producing visible light, the second endoscope including
means for exposing the part to ultraviolet light, the means for exposing extending from a first end of the second endoscope including an eyepiece toward a second end of the second endoscope, the second end of the second endoscope including an outlet for exposing the part to ultraviolet light, the outlet for exposing the part to ultraviolet light being open in a direction transverse to a longitudinal axis of the second endoscope, and
means for viewing the part exposed to ultraviolet light extending from the first end of the second endoscope to the second end and configured to transmit light from the second end of the endoscope to the eyepiece while the second endoscope is in the hole, the means for viewing being open at the second end of the endoscope in a direction transverse to the longitudinal axis of the second endoscope, and
wherein the pipes positioned inside the rod include an air pipe, a powder pipe, and a liquid pipe and extend from a first end of the rod to a second end of said rod opposite the first end of the rod and each pipe has a first end for connection to feed means, the powder and liquid pipes have respective opposite ends that open to an outside of the rod in a same direction as the light guide and the means for transmitting an image open, and the air pipe has an opposite end opening out axially at the second end of the rod to generate a flow of air for protecting the end of the first endoscope inside an orifice.

27. An apparatus for searching for and detecting defects on parts that are substantially inaccessible, being located behind a wall, the apparatus comprising:

a rigid tubular cylindrical rod configured to pass an endoscope through an orifice in the wall;
pipes received in the rod configured to deposit penetration test substances on a portion of the part under examination;
a light guide received in the rod and configured to illuminate the part under examination; and
first image transmission means received in the rod and configured to allow a user to observe said portion of the part under examination,
wherein the light guide and the first image transmission means comprise a first endoscope that operates solely with visible light mounted axially in the rod and that is adjacent to the pipes, said first endoscope includes a first tube in which the visible light guide and the first image transmission means are mounted in parallel, the first image transmission means has a diameter greater than that of the light guide, and
said first endoscope is free of any means for producing ultraviolet light; and
a second endoscope that operates solely with ultraviolet light, independent of the first endoscope and of said rod, configured to allow a user to observe the portion of the part that has been treated by the penetration test substances,
wherein said second endoscope is free of any pipe for depositing penetration test substances on said portion of the part under examination, and is free of any means for producing visible light, and
the second endoscope includes,
a first end provided with an eyepiece,
a second end opposite the first end and including a light outlet,
an ultraviolet light guide,
second image transmission means extending from the first end of the second endoscope along a longitudinal axis of the second endoscope toward the second end of the second endoscope and configured to transmit light to the eyepiece from behind said wall and through the orifice while the first end of the second endoscope is in front of said wall, and
a second tube with a cylindrical cross-section as viewed along a longitudinal axis of the ultraviolet light guide, the cylindrical cross-section located proximate to the second end, and the ultraviolet light guide and the second image transmission means being disposed within the second tube,
wherein the light guide of the first endoscope comprises an optical fiber cable extending from one end to the other of the first tube,
wherein the optical fiber cable has a bent outlet end oriented obliquely relative to the axis of the first tube and configured to be brought into the vicinity of a portion of the part that is to be illuminated in visible light,
wherein the first image transmission means comprise optical reflector means mounted at one end of the first tube on the optical axis of the image transmission means and oriented obliquely relative to said optical axis, and
wherein the optical reflector means and the bent outlet end of the optical fiber cable are adjacent and are oriented so as to illuminate and observe respectively a same portion of the part, wherein the pipes received inside the rod include an air pipe, a powder pipe, and a liquid pipe and extend from a first end of the rod to a second end of said rod opposite the first end of the rod, and each pipe has a first end for connection to feed means, the powder and liquid pipes have respective opposite ends that open to an outside of the rod in a same direction as the light guide and the first image transmission means open, and the air pipe has an opposite end opening out axially at the second end of the rod to generate a flow of air for protecting the end of the first endoscope inside the orifice.

28. A system for detecting defects in a turbojet engine comprising:

a set including a first endoscope and a second endoscope, which are used successively by being passed through an orifice in a wall for observing parts of the engine, the first endoscope comprising, pipes received in a rigid tubular cylindrical rod, the rod including a longitudinal axis and being configured to pass an endoscope through an orifice in the wall, a plurality of the pipes being configured to deposit penetration test substances on a portion of the part under examination;

a light guide received in the rod and configured to illuminate the part under examination; and first image transmission means received in the rod and configured to allow a user to observe said portion of the part under examination, wherein the light guide and first image transmission means each open in a direction transverse to the longitudinal axis of the rod, wherein the first endoscope operates solely with visible light and is mounted axially in the rod and is adjacent to the pipes, said first endoscope further includes a first tube in which the visible light guide and the first image transmission means are mounted in parallel, and the first image transmission means has a diameter greater than that of the light guide, and said first endoscope is free of any means for producing ultraviolet light; and wherein the second endoscope operates solely with ultraviolet light and is independent of the first endoscope and of said rod, wherein the second endoscope is configured to allow a user to observe the portion of the part that has been treated by the penetration test substances, wherein said second endoscope is free of any pipe for depositing penetration test substances on said portion of the part under examination, and is free of any means for producing visible light, and the second endoscope comprises, a first end provided with an eyepiece, a second end opposite the first end and including a light outlet, an ultraviolet light guide, second image transmission means extending from the first end of the second endoscope along a longitudinal axis of the second endoscope toward the second end of the second endoscope and configured to transmit light to the eyepiece from behind said wall and through the orifice while the first end of the second endoscope is in front of said wall, and a second tube with a cylindrical cross-section as viewed along a longitudinal axis of the ultraviolet light guide, the cylindrical cross-section located proximate to the second end, and the ultraviolet light guide and the second image transmission means being disposed within the second tube, wherein the ultraviolet light guide and second image transmission means open in a direction transverse to a longitudinal axis of the second endoscope, and wherein the pipes positioned inside the rod include an air pipe, a powder pipe, and a liquid pipe and extend from a first end of the rod to a second end of said rod opposite the first end of the rod and each pipe has a first end for connection to feed means, the powder and liquid pipes have respective opposite ends that open to an outside of the rod in a same direction as the light guide and the first image transmission means open, and the air pipe has an opposite end opening out axially at the second end of the rod to generate a flow of air for protecting the end of the first endoscope inside the orifice.

* * * * *